United States Patent [19]

Ishii et al.

[11] Patent Number: 5,919,486

[45] Date of Patent: Jul. 6, 1999

[54] POWDER PREPARATION AND A PROCESS FOR PREPARING THE SAME

[75] Inventors: Takanori Ishii; Nobuhiro Hasegawa; Masaaki Katsuro, all of Aichi; Kazumasa Suzuki, Kanagawa; Masumi Koishi, Hokkaido, all of Japan

[73] Assignee: San-Ei Sucrochemical Co., Ltd., Aichi, Japan

[21] Appl. No.: 08/867,406

[22] Filed: Jun. 2, 1997

Related U.S. Application Data

[63] Continuation of application No. 08/507,477, filed as application No. PCT/JP94/02246, Dec. 27, 1994, abandoned.

[30] Foreign Application Priority Data

Dec. 27, 1993 [JP] Japan ..................................... 5-346829

[51] Int. Cl.$^6$ ..................................................... A61K 9/14
[52] U.S. Cl. .......................................... 424/489; 424/490
[58] Field of Search ................................... 424/489, 490, 424/461, 46

[56] References Cited

U.S. PATENT DOCUMENTS

| | | | |
|---|---|---|---|
| 4,443,497 | 4/1984 | Samejima et al. | 427/213.36 |
| 5,190,775 | 3/1993 | Klose | 426/2 |
| 5,456,985 | 10/1995 | Zgoulli et al. | 428/402.2 |

FOREIGN PATENT DOCUMENTS

| | | |
|---|---|---|
| 0 182 296 | 5/1986 | European Pat. Off. . |
| 2-27944 | 1/1990 | Japan . |
| 5-112469 | 5/1993 | Japan . |
| WO/89/04842 | 6/1989 | WIPO . |

*Primary Examiner*—Thurman K. Page
*Assistant Examiner*—William E. Benston, Jr.
*Attorney, Agent, or Firm*—Smith, Gambrell & Russell, LLP; Beveridge, DeGrandi, Weilacher & Young Intellectual Property Group

[57] ABSTRACT

A liquid oil and fat ingredient or others are carried by pores of a porous carrier composed of porous starch grain obtained by reacting an enzyme having raw starch digestive activity onto the starch. With starch being used as porous carrier, the powder preparation according to the present invention is not harmful to the human body, it can be supplied continuously in great volumes, manufactured cheaply without difficult processing, and moreover, being completely biodegradable, this powder preparation does not cause any environmental problems. It can be used in various industrial fields.

18 Claims, No Drawings

POWDER PREPARATION AND A PROCESS FOR PREPARING THE SAME

This application is a continuation of application Ser. No. 08/507,477, filed Oct. 10, 1995, which application is entirely incorporated herein by reference, which is a 371 of PCT/JP94/02246 Filed Dec. 27, 1994.

TECHNICAL FIELD

The present invention relates to a powder preparation and a process for preparing the same and, more particularly, a powder preparation using a porous carrier obtained by making an enzyme having raw starch digestive activity to react on starch and a preparation process thereof.

Object substances or materials carried by the porous carrier in the powder preparation of the present invention comprise medicines, agricultural chemicals, fertilizers, pigments, paints, inks, biochemical products, oil and fat, foods, food additives, fragrances, cosmetics and other substances used in various industrial fields.

BACKGROUND ART

For powder preparations wherein a liquid object material is pulverized, there has been one wherein the object material is carried by various pulverizing bases including those based on petroleum.

Conventionally, petroleum base materials such as polyethylene glycol, polyvinyl alcohol, etc. have been largely used as pulverizing base.

Conventional powder preparations, however, present some inconveniences such as hard processing of pulverizing base, expensive production cost, difficulty of continuous and massive supply of pulverizing base and some faults of poor security of being injurious to the human body when massive pulverizing base is administrated or remaining permanently because they are not biodegradable, so they were far from being used largely and massively in various industrial fields.

For the reason of security, especially, the use of petroleum based powder preparations is limited in the field of foods, cosmetics, etc.

Hence, a powder preparation which would not be harmful to the human body, whose continuous and massive supply is assured and production cost is cheap, which needs no difficult processing, is completely biodegradable and can be largely used in various industrial fields has been desired.

DISCLOSURE OF THE INVENTION

The present inventors have conducted earnest researches on the powder preparations that would meet the conditions mentioned above and have invented the use of a porous carrier composed of porous starch grain wherein an enzyme having raw starch digestive activity is made to react on starch.

Then, using the porous carrier, they have tried to pulverize actually various materials that are generally considered hard to pulverize.

As the result, they have found that a porous carrier composed of porous starch grain obtained by reacting an enzyme having raw starch digestive activity on starch provides a large porous surface, that perforated starch presents better absorption of both water and oil and that materials of various state get into the pores under appropriate conditions and are carried by said pores, so as to accomplish finally the present invention.

Namely, the subject of the present invention can be attained by the following means.

First, a powder preparation, wherein a liquid oil and fat ingredient is carried by pores of a porous carrier composed of porous starch grain obtained by reacting an enzyme having raw starch digestive activity on starch.

Second, a powder preparation, wherein an aqueous solution ingredient in which an object material is dissolved is carried by pores of a porous carrier composed of porous starch grain obtained by reacting an enzyme having raw starch digestive activity on starch.

Third, a powder preparation, wherein an organic solvent ingredient in which an object material is dissolved is carried by pores of a porous carrier composed of porous starch grain obtained by reacting an enzyme having raw starch digestive activity on starch.

Fourth, a powder preparation, wherein an object material is carried by pores of a porous carrier composed of porous starch grain obtained by reacting an enzyme having raw starch digestive activity on starch.

Fifth, a powder preparation according to one of the first to fourth means mentioned above, wherein the same is put into a microcapsule by coating its surface.

Sixth, a process for preparing a powder preparation, wherein porous starch grain is obtained by reacting an enzyme having raw starch digestive activity on starch, the obtained porous starch grain is mixed with a liquid oil and carried.

Seventh, a process for preparing a powder preparation, wherein porous starch grain is obtained by reacting an enzyme having raw starch digestive activity on starch, then the obtained porous starch grain is mixed with an aqueous solution where an object material is dissolved, and carried.

Eighth, a process for preparing a powder preparation, wherein porous starch grain is obtained by reacting an enzyme having raw starch digestive activity on starch, then the obtained porous starch grain is mixed with an organic solvent where an object material is dissolved, and carried.

Ninth, a process for preparing a powder preparation, wherein a porous carrier composed of porous starch grain is obtained by reacting an enzyme having raw starch digestive activity on starch, the obtained porous carrier and an object material are dispersed in a solvent in which the object material does not dissolve, then the solvent is removed to carry the object material in the pores of the porous carrier.

Tenth, a process for preparing a powder preparation, wherein a porous carrier composed of porous starch grain is obtained by reacting an enzyme having raw starch digestive activity on starch, the obtained porous carrier and an object material are dispersed in a solvent in which the object material can dissolve, then the solvent is removed to carry the object material in the pores of the porous carrier.

Eleventh, a process for preparing a powder preparation, wherein a porous carrier composed of porous starch grain is obtained by reacting an enzyme having raw starch digestive activity on starch, the obtained porous carrier is mixed with an object material, and carried.

Twelfth, a process for preparing a powder preparation for preparing a microcapsule of the powder preparation which comprises the steps of preparing the powder preparation according to one of the sixth to eleventh means mentioned above, dispersing the same in a coating solution and drying and forming a coating layer on the surface.

Thirteenth, a process for preparing a powder preparation for preparing microcapsule of the powder preparation which comprises the steps of preparing the powder preparation according to one of the sixth to eleventh means mentioned above, emulsifying the same in a coating solution and drying and forming a coating layer on the surface.

Fourteenth, a process for preparing a powder preparation for preparing microcapsule of the powder preparation which comprises the steps of preparing the powder preparation according to one of the sixth to eleventh means mentioned above, spraying a coating agent to form a coating layer on the surface.

Fifteenth, a process for preparing a powder preparation, wherein a porous starch grain is obtained by reacting an enzyme having raw starch digestive activity on starch, the obtained porous starch grain is mixed with a solution containing the object material to form a powder preparation, and wherein a coating layer is formed on the surface of the obtained powder preparation.

Here, the porous carrier may be prepared according to the process described in the Japanese TOKKAIHEI 5-112469 [TOKKYO-KOKAI-KOHO (18 months Publication of Unexamined Patent Application) HEISEI 5(1993)-112469] by the present inventors.

Then, an object material may be microcenapsulated by making pores of a porous carrier carry the object material and coating the surface thereof with a coating agent to form a coating layer.

Additionally, the release of the object material can be controlled and the taste can be improved by pulverizing an object material of various industrial fields through blending or other processing with the porous carrier and then microencapsulating the same through the coating process.

Zein, hydroxypropylmethylcellulose phthalate or others may be used as coating agent.

The coating may be realized by dispersing or emulsifying the powder preparation in a coating solution where coating agent is dissolved and then drying the same through spray drying, lyophilizing or other drying method, or by spray cooling coating agent such as vegetable hardened oil, carnauba wax, etc.

With starch being used as porous carrier, the powder preparation according to the present invention is not harmful to the human body. It can be supplied continuously in great volume, manufactured cheaply without difficult processing and moreover, it is completely biodegradable which does not incur any environmental problems. It will be used largely in various industrial fields.

Best Mode for Carrying Out the Invention

Hereinbelow, each Example of the present invention will be explained in detail.

EXAMPLE 1

First, the preparation of the porous carrier will be disclosed.

100 g of corn starch and 1.0 g of Dabiase K-27 (Trade name: raw starch digestive enzyme made by Daikin Kogyo Co., Ltd.) were put in 1000 ml of acetic acid buffer solution of 0.25 mM (pH 5.0) and stood overnight at 40° C. while stirring and then washed and dried to obtain porous carrier composed of porous corn starch grain.

100 g of the porous carrier obtained by the process mentioned above and 75 g of soybean oil were mixed by Twinmix-08 made by Dalton Co., Ltd.

In this manner, an oil and fat having a very fluid powder form was produced.

In comparison, 100 g of corn starch and 75 g of soybean oil were mixed by Twinmix-08 made by Dalton Co., Ltd. only to obtain the same product having a paste form.

EXAMPLE 2

100 g of the porous carrier obtained in the Example 1 and 135 g of soy sauce (dark soy sauce made by Kikkoman Corp.) were mixed using Twinmix-08 of Dalton Co., Ltd. to obtain a fluid, scarcely sticky powder preparation of soy sauce.

In comparison, 100 g of corn starch and 135 g of soy sauce were mixed using Twinmix-08 made by Dalton Co., Ltd. only to obtain the same product having a paste form.

EXAMPLE 3

100 g of the porous carrier obtained in the Example 1 and 80 g of a liquid fragrance ("Meijiya's Essence Orange" made by Meijiya Co., Ltd.) were mixed using Twinmix-08 made by Dalton Co., Ltd. to obtain a fluid, scarcely sticky powder preparation of fragrance.

In comparison, 100 g of corn starch and 80 g of fragrance were mixed using Twinmix-08 made by Dalton Co., Ltd. only to obtain the same product having a paste form.

EXAMPLE 4

13.5 g of the porous carrier obtained in the Example 1 and 1.5 g of red pigment powder (Sekishoku No. 102) were mixed (1000 rpm, 10 min.) by Mechanomill (trade name: Okada Seikou Co., Ltd.).

When the mixed product obtained was observed through a scanning electron microscope, the Sekishoku No. 102 was carried in the pores of the porous carrier and became powder preparation.

9.98 g of corn starch was added to 0.02 g of the mixed product obtained (containing 0.002 g of Sekishoku No. 102) and mixed by Spatula for 30 seconds.

In comparison, 9.998 g of corn starch was added to 0.002 g of Sekishoku No. 102 and treated similarly as before.

The absolute volume of Sekishoku No. 2 ought to be same in both samples.

Each of the two (2) samples was sampled 5 times respectively and their absorbance was determined.

510 nm was adopted as measuring wave length.

An calibration curve showing the relationship between the absorbance and the dilution multiplying factor had been established beforehand and the dilution multiplying factor was calculated from the measured absorbance.

The theoretical dilution multiplying factor also was calculated for the sampling volume.

The ratio of the theoretical dilution multiplying factor and the dilution multiplying factor obtained from the actual measured value was calculated and the variance of this ratio was compared.

If this variance is small, Sekishoku No. 102 may be considered uniformly mixed through the corn starch.

As the result, the variance was 0.252 when Sekishoku No. 102 was added and mixed with corn starch while it was 0.004 when the porous carrier obtained in the Example 1 was used.

The variance was significantly smaller when the porous carrier obtained in the Example 1 was used and, consequently, Sekishoku No. 102 may be considered to have been mixed uniformly.

This fact shows that the porous carrier obtained in the Example 1 may be advantageously used when a trace of additive ingredient should be mixed uniformly.

EXAMPLE 5

100 g of porous carrier obtained in the Example 1 and 20 g of ground 2,4-D (2,4-Dichlorophenoxy acetic acid) were dispersed in 500 ml of water (2,4-D being hardly dissolved at this moment), the solution was dehydrated by suction filtering and the residue after filtration was dried.

The obtained sample was observed by a scanning electron microscope to find that 2,4-D was buried and carried by pores of the porous carrier. When the product was applied to paddy-rice or lawn as herbicide, the release control effect thereof was observed.

EXAMPLE 6

As the present invention group, 20 g of naphthalene was dissolved in 500 ml of 99% ethanol, and 50 g of porous carrier obtained in the Example 1 was added thereto and the solution was stirred for 1 minute, filtered under the reduced pressure and the residue after filtration was recovered.

The residue after filtration was spread over a Petri dish, left at 60° C. in a constant-temperature dryer and the remaining amount of naphthalene was determined with time.

Supposing the initial amount was 100, Table 1 shows the result of comparing the remaining amount naphthalene at respective time lapses of the storage with the control group wherein only naphthalene is spread over a Petri dish.

TABLE 1

|  | Initial | 1 hour | 2 hours | 3 hours | 24 hours |
| --- | --- | --- | --- | --- | --- |
| Control group | 100.00 | 79.39 | 63.71 | 47.99 | 0.00 |
| Invention group | 100.00 | 94.38 | 88.16 | 83.23 | 25.42 |

According to the results of Table 1, the use of a porous carrier obtained in the Example 1 may improve the continuous effect of naphthalene.

EXAMPLE 7

100 g of porous carrier obtained in the Example 1, 20 g of soybean peptide powder ("Hainyuto PM" made by Fuji Seiyu Co, Ltd.) and 1000 ml (solid concentration of 6%) of corn gluten mill extract by 70% ethanol (zein) were stirred and mixed for 1 (one) minute at 14700 rpm by means of a Warring blender (type 7011G) to obtain a emulsion, then the emulsion was spray-dried by means of a spray-dryer (SD-1 made by Tokyo Rika) to obtain microcapsule wherein soy peptide is carried by pores of the porous carrier and the surface is covered with zein coating layer.

1 g of the microcapsule was dispersed in 1 (one) liter of water, the absorbance was determined at 270 nm and the elution rate of soy peptide was estimated, which was found to be 20.3%.

Moreover, 10 subjects tasted the microcapsule of the invention and soy peptide powder and all (ten) of them found soy peptide bitter while 8 of them found the microcapsule not bitter.

The results mentioned above suggest that bitter substance can be masked by coating with zein through the usage of porous carrier obtained in the Example 1.

We claim:

1. A powder preparation comprising a porous starch grain carrier formed by reacting a starch grain with an enzyme having starch digestive activity on starch, and a material carried within the pores of said porous starch grain carrier.

2. A powder preparation according to claim 1, wherein said material is a liquid oil and fat ingredient.

3. A powder preparation according to claim 1, wherein said material is dissolved in an aqueous solution.

4. A powder preparation according to claim 1, wherein said material is dissolved in an organic solvent.

5. A powder preparation according to claim 1 wherein said carrier and said material are microencapsulated within a coating about the surface of said carrier.

6. A powder preparation according to claim 1, wherein said material is selected from the group consisting of medicines, agricultural chemicals, fertilizers, pigments, paints, inks, biochemical products, oils and fats, foods, food additives, fragrances, cosmetics and industrial chemicals.

7. A process for preparing a powder preparation comprising subjecting a starch grain to an enzyme having starch digestive activity on starch for a period of time sufficient for said enzyme to form a plurality of pores in said starch grain, mixing said starch grain with a material and permitting said material to enter said pores on said starch grain whereby said material is carried by said pores of said starch grain.

8. A process for preparing a powder preparation according to claim 7, wherein said material is a liquid oil.

9. A process for preparing a powder preparation according to claim 7, wherein said Material is dissolved in an aqueous solution.

10. A process for preparing a powder preparation according to claim 7, wherein said material is dissolved in an organic solvent.

11. A process for preparing a powder preparation according to claim 7, wherein said porous starch grain and material are dispersed in a solvent in which said material does not dissolve, and then removing said solvent whereby said material remains in the pores of said porous starch grain.

12. A process for preparing a powder preparation according to claim 7, wherein the porous starch grain and material are dispersed in a solvent in which said material can dissolve, and then removing said solvent whereby said material remains in said pores of said porous starch grain.

13. A process for preparing a powder preparation according to claim 7 comprising the further steps of dispersing said porous starch grain having said material carried by said pores of said starch grain in a coating solution and then drying said coating solution whereby a coating layer is formed on the surface of said porous starch grain to microencapsulate said grain and said material within the pores of said grain.

14. A process for preparing a powder preparation according to claim 7 comprising the further steps of emulsifying said porous starch grain having said material carried by said pores of said starch grain in a coating solution and then drying said coating solution whereby a coating layer is formed on the surface of said porous starch grain to microencapsulate said grain and said material within the pores of said grain.

15. A process for preparing a powder preparation according to claim 7 comprising the further steps of spraying said porous starch grain having said material carried by said pores of said starch grain with a coating solution and then drying said coating solution whereby a coating layer is formed on the surface of said porous starch grain to microencapsulate said grain and said material within the pores of said grain.

16. A process according to claim 7, wherein said material is selected from the group consisting of medicines, agricultural chemicals, fertilizers, pigments, paints, inks, biochemical products, oils and fats, foods, food additives, fragrances, cosmetics and industrial chemicals.

17. A process for preparing a powder preparation comprising forming a porous carrier comprising a plurality of porous starch grains, by subjecting said starch grains to an enzyme having a raw starch digestive activity on starch for a period of time sufficient for said enzyme to form a plurality of pores in said starch grains, mixing said porous carrier with a material and permitting said material to enter said pores in said porous carrier whereby said material is carried by said pores of said porous carrier.

18. A process according to claim 17, wherein said material is selected from the group consisting of medicines, agricultural chemicals, fertilizers, pigments, paints, inks, biochemical products, oils and fats, foods, food additives, fragrances, cosmetics and industrial chemicals.

* * * * *